US00PP21887P2

(12) United States Plant Patent
van de Meer

(10) Patent No.: US PP21,887 P2
(45) Date of Patent: Apr. 26, 2011

(54) ***ASTILBE* PLANT NAMED 'PURPLE RAIN'**

(50) Latin Name: *Astilbe chinensis*
Varietal Denomination: Purple Rain

(75) Inventor: Hans van de Meer, Roelofarendsveen (NL)

(73) Assignee: Compass Plants B.V., Hillegom (NL)

( * ) Notice: Subject to any disclaimer, the term of this patent is extended or adjusted under 35 U.S.C. 154(b) by 0 days.

(21) Appl. No.: 12/653,765

(22) Filed: Dec. 16, 2009

(51) Int. Cl.
*A01H 5/00* (2006.01)

(52) U.S. Cl. ..... Plt./407

(58) Field of Classification Search ..... Plt./407
See application file for complete search history.

*Primary Examiner* — June Hwu

(74) *Attorney, Agent, or Firm* — C. A. Whealy

(57) ABSTRACT

A new and distinct cultivar of *Astilbe* plant named 'Purple Rain', characterized by its compact, upright and outwardly spreading plant habit; strong dark-colored foliage; freely and uniformly flowering habit with inflorescences positioned above the foliar plane; purple-colored flowers; and good garden performance.

2 Drawing Sheets

Botanical designation: *Astilbe chinensis*.
Cultivar denomination: 'PURPLE RAIN'.

BACKGROUND OF THE INVENTION

The present invention relates to a new and distinct cultivar of *Astilbe* plant, botanically known as *Astilbe chinensis* and hereinafter referred to by the name 'Purple Rain'.

The new *Astilbe* plant is a product of a planned breeding program conducted by the Inventor in Roelofarendsveen, The Netherlands. The objective of the breeding program was to create new compact *Astilbe* plants with attractive foliage and flower coloration.

The new *Astilbe* plant originated from a cross-pollination made by the Inventor in 1998 in Roelofarendsveen, The Netherlands, of two unnamed seedling selections of *Astilbe chinensis*, not patented. The new *Astilbe* plant was discovered and selected by the Inventor as a single flowering plant within the progeny of the stated cross-pollination in a controlled greenhouse environment in Roelofarendsveen, The Netherlands in 2000.

Asexual reproduction of the new *Astilbe* plant by divisions in a controlled environment in Roelofarendsveen, The Netherlands since December, 2003, has shown that the unique features of this new *Astilbe* plant are stable and reproduced true to type in successive generations.

SUMMARY OF THE INVENTION

Plants of the new *Astilbe* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Purple Rain'. These characteristics in combination distinguish 'Purple Rain' as a new and distinct cultivar of *Astilbe:*

1. Compact, upright and outwardly spreading plant habit.
2. Strong dark-colored foliage.

3. Freely and uniformly flowering habit with inflorescences positioned above the foliar plane.
4. Purple-colored flowers.
5. Good garden performance.

Plants of the new *Astilbe* differ primarily from plants of the parent selections in the following characteristics:

1. Plants of the new *Astilbe* are more compact than plants of the parent selections.
2. Plants of the new *Astilbe* are more freely flowering than plants of the parent selections.

Plants of the new *Astilbe* can be compared to plants of *Astilbe chinensis* 'Pumila', not patented. In side-by-side comparisons conducted in Roelofarendsveen, The Netherlands, plants of the new *Astilbe* differed from plants of 'Pumila' in the following characteristics:

1. Plants of the new *Astilbe* were taller than plants of 'Pumila'.
2. Leaves of plants of the new *Astilbe* were glossier than leaves of plants of 'Pumila'.
3. Plants of the new *Astilbe* were more freely flowering than plants of 'Pumila'.
4. Plants of the new *Astilbe* and 'Pumila' differed in flower color.
5. Plants of the new *Astilbe* were more sunlight-resistant than plants of 'Pumila'.

BRIEF DESCRIPTION OF THE PHOTOGRAPHS

The accompanying colored photographs illustrate the overall appearance of the new *Astilbe* plant, showing the colors as true as it is reasonably possible to obtain in colored reproductions of this type. Colors in the photographs may differ slightly from the color values cited in the detailed botanical description which accurately describe the colors of the new *Astilbe* plant.

The photograph on the first sheet comprises a side perspective view of a typical flowering plant of 'Purple Rain' grown in a container.

The photograph at the top of the second sheet is a close-up view of typical inflorescences of 'Purple Rain'.

The photograph at the bottom of the second sheet is a close-up view of the upper surface of a typical leaf of 'Purple Rain'.

DETAILED BOTANICAL DESCRIPTION

The aforementioned photographs and following observations, measurements and values describe plants grown in 1.5-liter containers in an outdoor nursery in Roelofarendsveen, The Netherlands, under commercial practice during the summer. During the production of the plants, day temperatures ranging from 12° C. to 32° C. and night temperatures ranging from 4° C. to 16° C. Plants were 1.5 years old when the photographs and description were taken. In the following description, color references are made to The Royal Horticultural Society Colour Chart, 2007 Edition, except where general terms of ordinary dictionary significance are used.

Botanical classification: *Astilbe chinensis* 'Purple Rain'.

Parentage:

*Female, or seed, parent.*—Unnamed seedling selection of *Astilbe chinensis*, not patented.

*Male, or pollen, parent.*—Unnamed seedling selection of *Astilbe chinensis*, not patented.

Propagation:

*Type.*—By divisions.

*Time to initiate roots.*—About three weeks at 20° C.

*Root description.*—Thick, fleshy; brown in color.

*Rooting habit.*—Dense.

Plant description:

*Plant form/habit.*—Herbaceous perennial; compact, upright and outwardly spreading plant habit; inverted broadly triangular in shape; flowering stems and leaves basal; dense and bushy growth habit; low to moderate vigor; freely and uniformly flowering with numerous flowers on branched panicles positioned above the foliar plane.

*Growth rate.*—Moderate; from divisions, about 28 weeks are required to produce fully-gown flowering plants.

*Plant height* (*soil level to top of foliar plane*).—About 28.4 cm.

*Plant height* (*soil level to top of inflorescences*).—About 44.2 cm.

*Plant width* (*spread*).—About 48.3 cm.

*Stem description.*—Length: About 16.1 cm. Diameter: About 5 mm. Internode length: About 6.1 cm. Strength: Strong. Texture: Densely pubescent. Color: Close to 146B to 146C.

Foliage description:

*Arrangement.*—Alternate; biternately compound.

*Leaf length* (*excluding petiole*).—About 20.6 cm.

*Leaf width.*—About 22.3 cm.

*Lateral leaflet length.*—About 3.7 cm.

*Lateral leaflet width.*—About 2.4 cm.

*Terminal leaflet length.*—About 4.2 cm.

*Terminal leaflet width.*—About 3.4 cm.

*Lateral and terminal leaflet shape.*—Ovate to broadly ovate.

*Lateral and terminal leaflet apex.*—Acute.

*Lateral and terminal leaflet base.*—Cordate to hastate.

*Lateral and terminal leaflet margin.*—Biserrate.

*Lateral and terminal leaflet texture, upper and lower surfaces.*—Sparsely pubescent.

*Lateral and terminal leaflet venation pattern.*—Pinnate.

*Lateral and terminal leaflet color.*—Developing leaves, upper surface: Close to 137B. Developing leaves, upper surface: Close to 138A. Fully expanded leaves, upper surface: Close to N137B; venation, close to 144A. Fully expanded leaves, lower surface: Close to 137A; venation, close to 147C.

*Leaf petiole length.*—About 8.8 cm.

*Leaf petiole diameter.*—About 3 mm.

*Leaflet petiole length.*—About 2 mm.

*Leaflet petiole width.*—About 1 mm.

*Leaf and leaflet petiole texture, upper and lower surfaces.*—Smooth, glabrous.

*Leaf and leaflet petiole color, upper and lower surfaces.*—Close to 144A to 144B.

Flower description:

*Flower type/habit.*—Numerous single rotate flowers arranged on terminal branched panicles; flowers face upright, outward or downward depending on position on the panicle; panicles narrowly triangular in shape; freely and uniformly flowering habit with about 1,000 flowers and flower buds per inflorescence.

*Fragrance.*—Faintly fragrant; sweet.

*Natural flowering season.*—Continuously flowering during the summer to late summer in The Netherlands.

*Postproduction longevity.*—Flowers last about ten days on the plant; flowers persistent.

*Flower buds.*—Height: About 1.5 mm. Diameter: About 1 mm. Shape: Broadly ovate. Color: Close to 71A.

*Inflorescence height.*—About 18.5 cm.

*Inflorescence diameter.*—About 8.9 cm.

*Flower diameter.*—About 4 mm.

*Flower depth.*—About 3.5 mm.

*Petals.*—Quantity per flower: Typically five in a single whorl. Length: About 2 mm. Lobe width: About 0.5 mm. Shape: Oblanceolate. Apex: Broadly acute. Margin: Entire. Texture, upper and lower surfaces: Smooth, glabrous. Color: Developing petals, upper and lower surfaces: Close to 84B. Fully expanded petals, upper and lower surfaces: Close to 75A; color becoming closer to 76B to 76C with development.

*Sepals.*—Quantity per flower: Typically five in a single whorl, fused towards the base; campanulate calyx. Length: About 1.5 mm. Width: About 0.5 mm. Shape: Ovate. Apex: Acute. Base: Cuneate, fused. Margin: Entire. Texture, upper and lower surfaces: Smooth, glabrous. Color: Developing sepals, upper and lower surfaces: Close to 71A. Fully developed sepals, upper and lower surfaces: Close to 182C; towards the margins, close to 71B to 71C.

*Peduncles.*—Length: About 23.3 cm. Diameter: About 2.5 mm. Angle: Erect. Strength: Strong. Texture: Smooth, glabrous. Color: Close to 152A.

*Pedicels.*—Length: About 0.5 mm. Diameter: About 0.4 mm. Angle: Erect to about 45° from vertical. Strength: Moderately strong. Texture: Smooth, glabrous. Color: Close to 182C.

*Reproductive organs.*—Stamens: Quantity per flower: Typically ten; anthers basifixed. Filament length: About 1 mm. Anther shape: Ovate. Anther length: About 0.3 mm. Anther color: Close to 158D. Pollen amount: Scarce. Pollen color: Close to 155D. Pistils: Quantity per flower: Two. Pistil length: About 0.2 mm. Style length: About 0.1 mm. Style color: Close to 68A. Stigma shape: Club-shaped. Stigma color: Close to 182D. Ovary color: Close to 156A.

*Seed/fruit.*—Seed and fruit development have not been observed.

Disease/pest resistance: Plants of the new *Astilbe* have not been noted to be resistant to pathogens and pests common to *Astilbe.*

Garden performance: Plants of the new *Astilbe* have been observed to have good garden performance and tolerate sunlight, rain, wind and temperatures ranging from about −30° C. to about 35° C.

It is claimed:

1. A new and distinct *Astilbe* plant named 'Purple Rain' as illustrated and described.

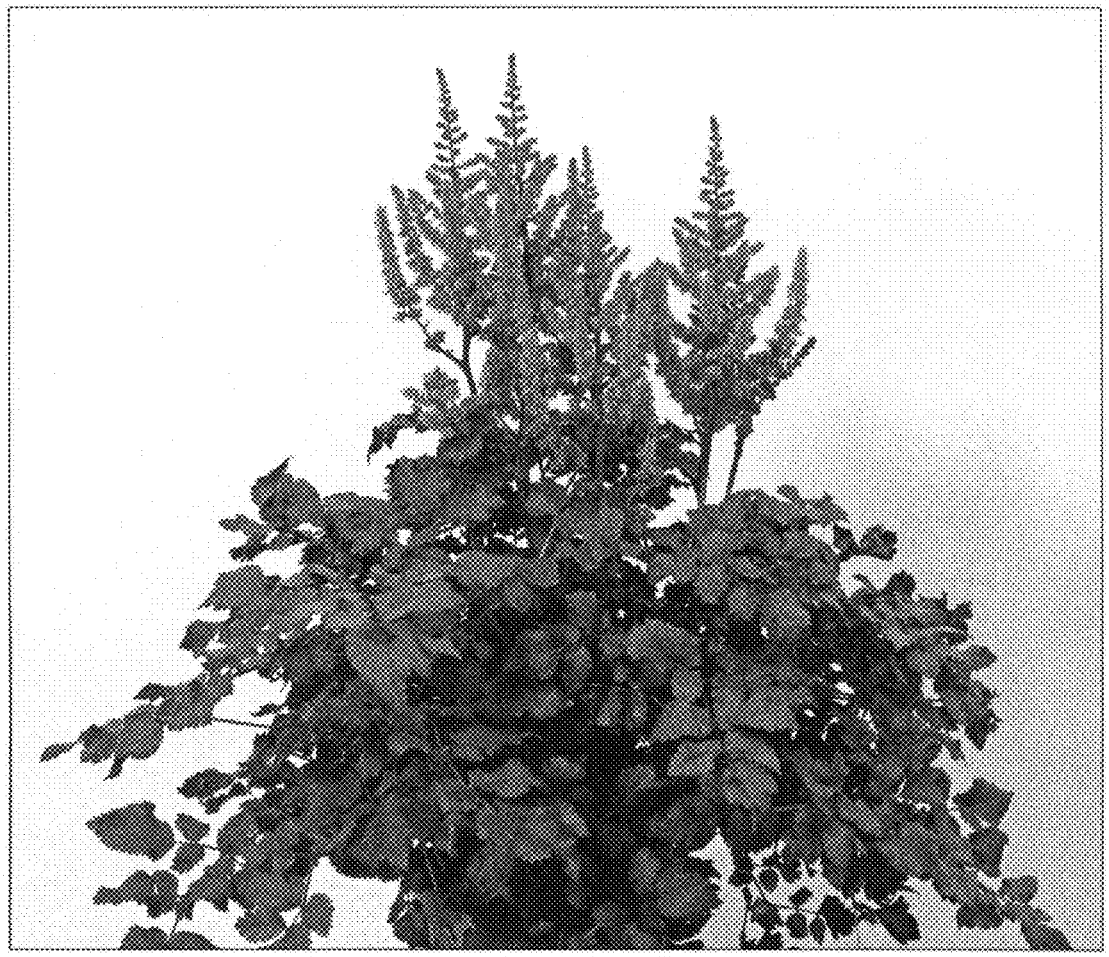

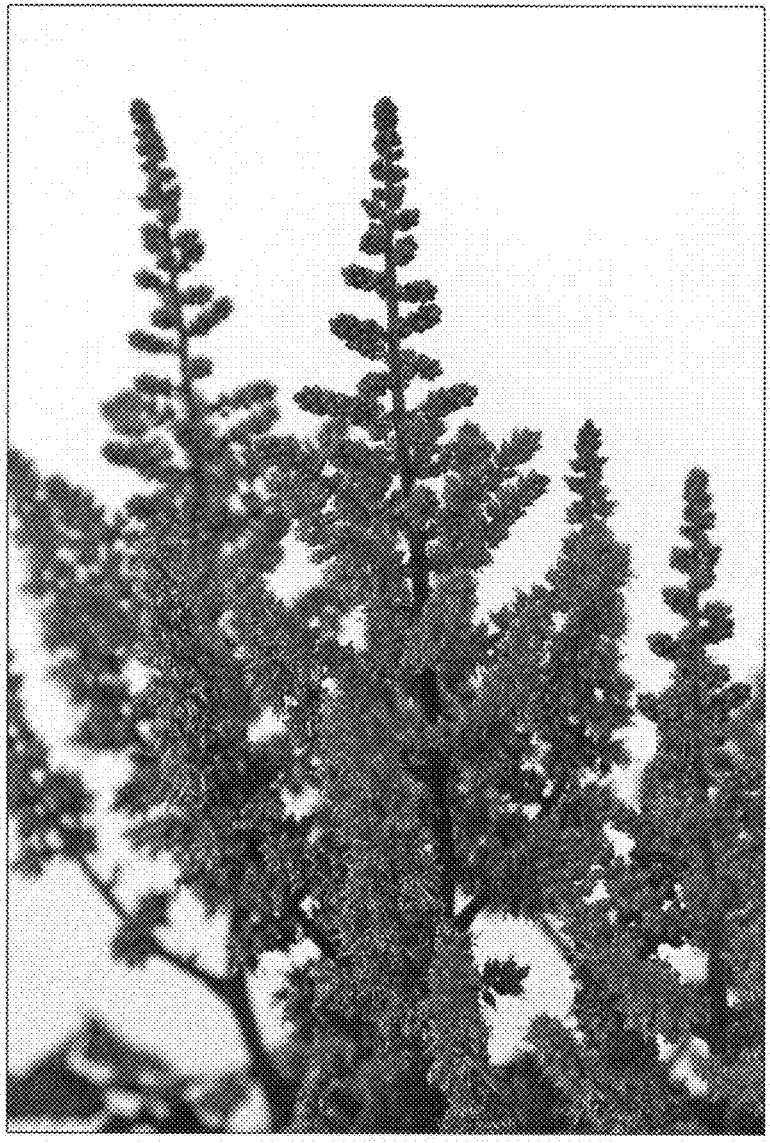
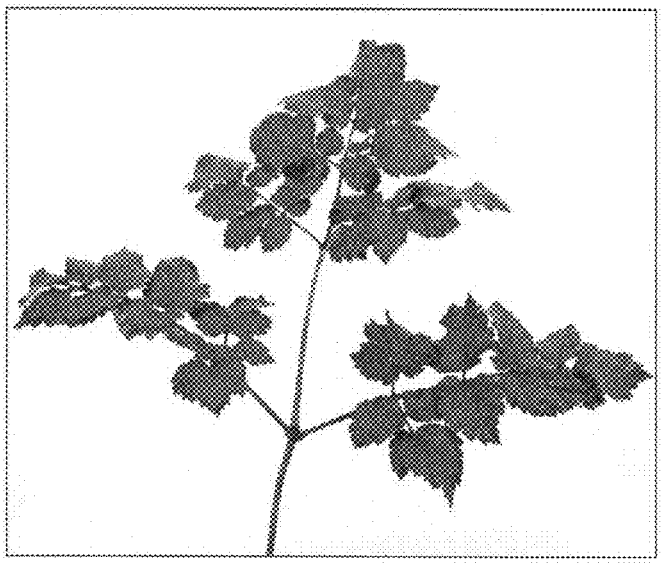

* * * * *